(12) United States Patent
Tanaka et al.

(10) Patent No.: US 9,757,208 B2
(45) Date of Patent: Sep. 12, 2017

(54) MEDICAL OR DENTAL HANDPIECE

(71) Applicant: J. MORITA MFG. CORP., Kyoto-shi, Kyoto (JP)

(72) Inventors: Hitoshi Tanaka, Kyoto (JP); Shozo Nakayama, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 0 days.

(21) Appl. No.: 15/333,890

(22) Filed: Oct. 25, 2016

(65) Prior Publication Data
US 2017/0035530 A1 Feb. 9, 2017

Related U.S. Application Data

(63) Continuation of application No. 13/083,336, filed on Apr. 8, 2011, now Pat. No. 9,510,917.

(30) Foreign Application Priority Data

Apr. 9, 2010 (JP) .................................. 2010-090564

(51) Int. Cl.
| | | |
|---|---|---|
| *A61C 1/12* | (2006.01) | |
| *A61C 1/18* | (2006.01) | |
| *A61C 1/06* | (2006.01) | |
| *A61B 17/00* | (2006.01) | |
| *A61B 17/32* | (2006.01) | |

(52) U.S. Cl.
CPC .............. *A61C 1/185* (2013.01); *A61B 17/00* (2013.01); *A61C 1/06* (2013.01); *A61C 1/12* (2013.01); *A61B 17/32002* (2013.01); *Y10T 74/19679* (2015.01)

(58) Field of Classification Search
CPC ..... A61B 17/32002; A61B 17/00; A61C 1/06; A61C 1/12; A61C 1/185; Y10T 74/19679
USPC ....... 433/131, 133, 114, 103, 124, 132, 462, 433/466; 74/460, 462, 466
See application file for complete search history.

(56) References Cited

U.S. PATENT DOCUMENTS

| | | |
|---|---|---|
| 2,226,145 A | 12/1940 | Smith |
| 2,813,337 A | 11/1957 | Uhler |
| 2,923,060 A | 2/1960 | Staunt |
| 4,278,428 A | 7/1981 | Straihammer et al. |

(Continued)

FOREIGN PATENT DOCUMENTS

| | | |
|---|---|---|
| EP | 2008609 A1 | 12/2008 |
| JP | S55-91348 A | 7/1980 |

(Continued)

*Primary Examiner* — Cris L Rodriguez
*Assistant Examiner* — Mirayda A Aponte
(74) *Attorney, Agent, or Firm* — Capitol City TechLaw

(57) ABSTRACT

A medical or dental handpiece has a grip. The grip includes first to third rotation shafts. The first and second shafts are connected through a first gear mechanism and the second and third shafts are connected through a second gear mechanism so that a rotation is transmitted from the first shaft through the first gear mechanism to the second shaft and then from the second shaft through the second gear mechanism to the third shaft. The first or second gear mechanism has an internal gear secured on one shaft and an external gear secured on the other shaft, the internal and the external gears being engaged with each other. The external gear is substantially enclosed within a cylindrical plane extending along a peripheral edge of the internal gear.

11 Claims, 7 Drawing Sheets

(56) References Cited

U.S. PATENT DOCUMENTS

| | | |
|---|---|---|
| 4,279,596 A | 7/1981 | Weber |
| 4,325,696 A | 4/1982 | Rosenstatter et al. |
| 5,281,138 A | 1/1994 | Rosenstatter |
| 7,179,087 B2 | 2/2007 | Kuhn |
| 7,556,498 B2 | 7/2009 | Schatz |
| 2003/0207233 A1* | 11/2003 | Lingenhole ............... A61C 1/06 433/131 |
| 2007/0275349 A1 | 11/2007 | Korytkowski |
| 2008/0318185 A1 | 12/2008 | Mizunuma et al. |
| 2010/0009312 A1* | 1/2010 | Maitre ................ A61B 17/162 433/131 |
| 2010/0077882 A1 | 4/2010 | Schreiber |

FOREIGN PATENT DOCUMENTS

| | | |
|---|---|---|
| JP | H07-51136 B2 | 6/1995 |
| JP | 2005-42883 A | 2/2005 |
| JP | 2005-520580 A | 7/2005 |
| JP | 2009-28512 A | 2/2009 |

* cited by examiner

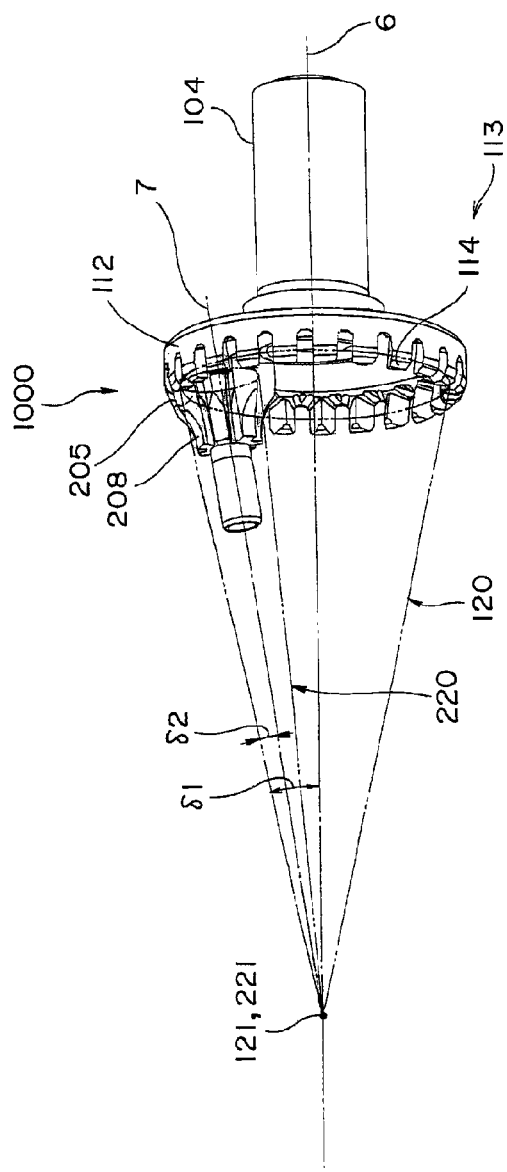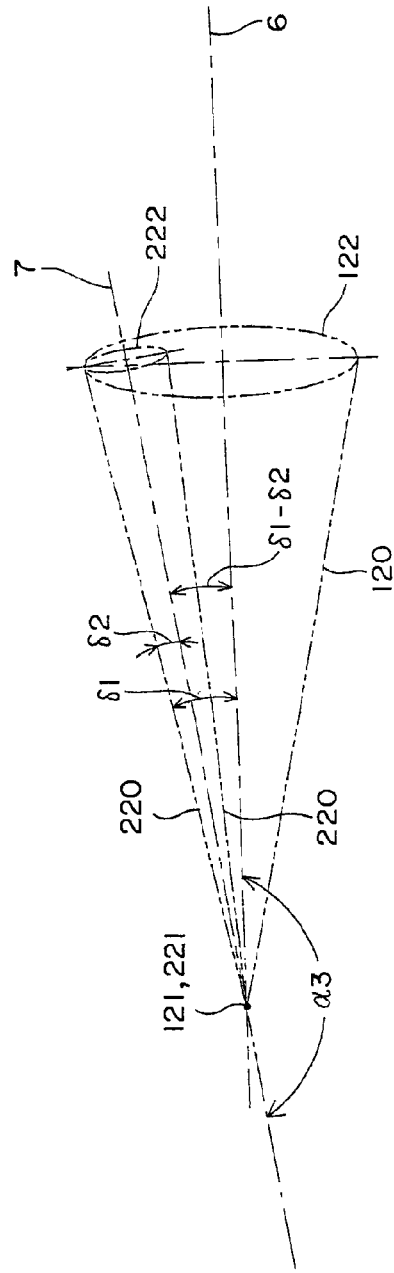
Fig. 5A
Fig. 5B

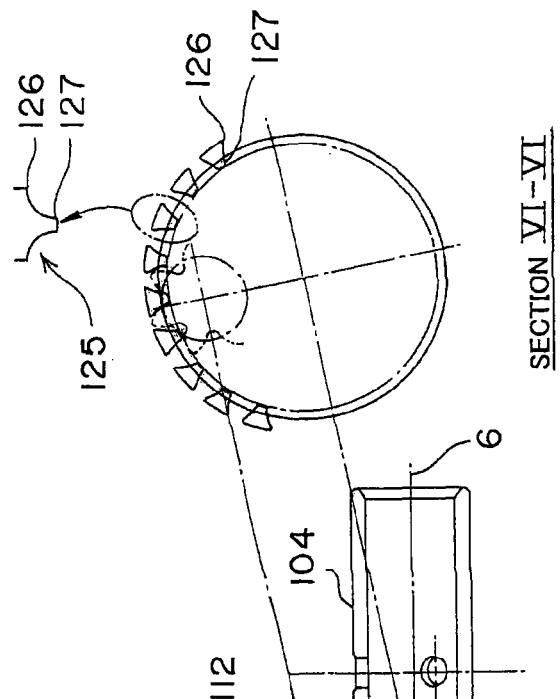
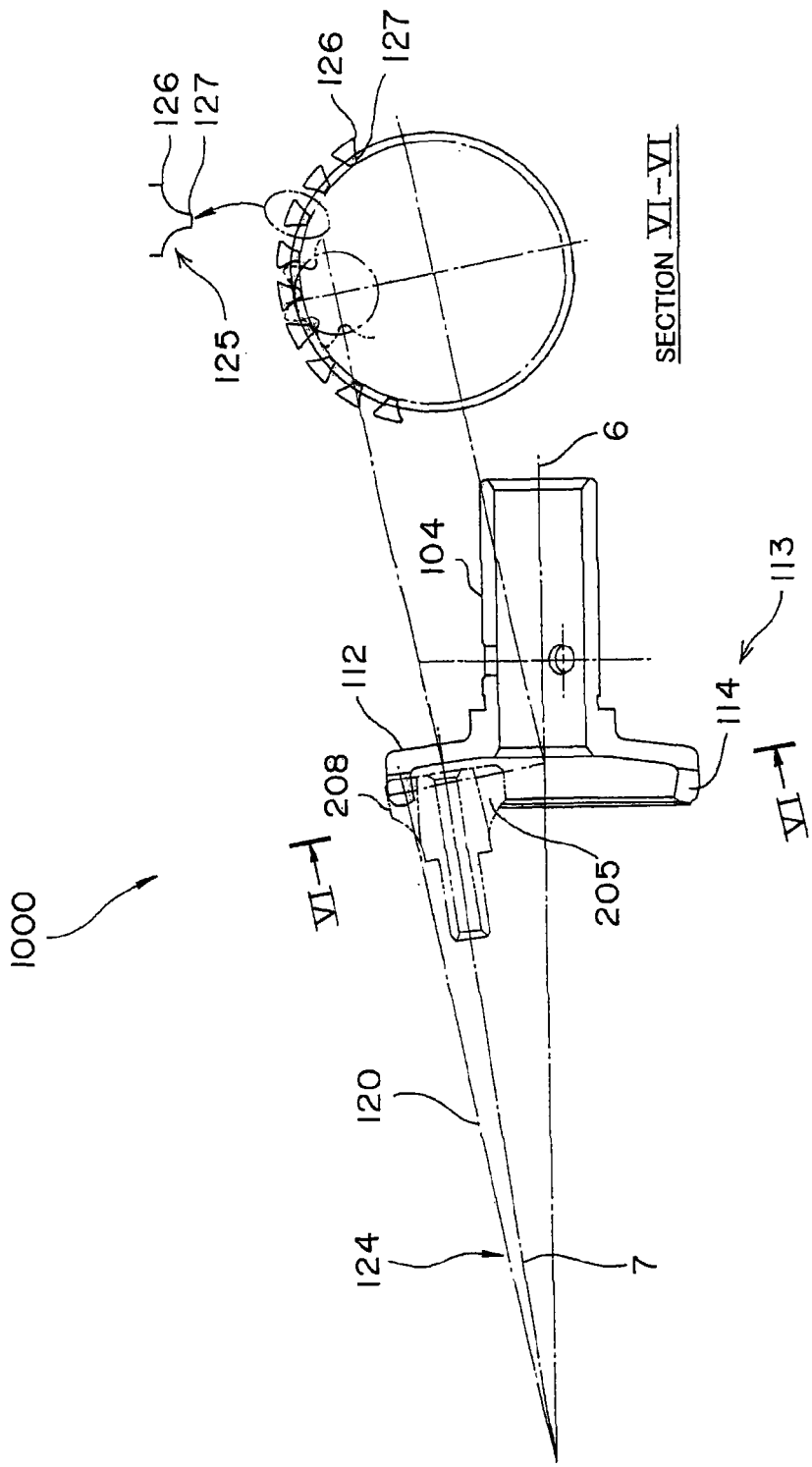

MEDICAL OR DENTAL HANDPIECE

This application is a continuation application of U.S. patent application Ser. No. 13/083,336 filed Apr. 8, 2011, the entire content of which is incorporated herein by reference. This application claims priority under 35 USC §119(a)-(d) to Japanese Patent Application No. 2010-090564 filed Apr. 9, 2010, the entire content of which is incorporated herein by reference.

FIELD OF THE INVENTION

The present invention relates to a medical or dental handpiece. In particular, the present invention relates to a medical or dental contra-angle handpiece.

BACKGROUND OF THE INVENTION

Conventionally, there has been known a motor-driven, medical or dental contra-angle handpiece. The handpiece has an external cylindrical grip portion and a drive source detachably connected to the proximal end of the grip portion. The distal end of the grip portion has a head in which a treatment or cutting tool is releasably attached. The grip portion is contra-angled so that distal and proximal central axes thereof cross with each other at a certain small angle as shown in JP 2005-520580 A, JP 2009-28512 A, JP 7-51136 B, and JP 2005-42883 A, for example.

The handpieces disclosed in JP 2005-520580 A and JP 7-51136 B are three-stage rotational speed increasing handpiece. According to this handpiece, the rotation from the drive source is transmitted to the first rotation shaft within the external cylinder. The rotation is increased by a pair of engaging gears and transmitted to the second rotation shaft. Further, the rotation is increased by another pair of gears and then transmitted to the third rotation shaft. Furthermore, the rotation is increased and then transmitted to the head potion for driving the treatment tool.

The handpiece disclosed in JP 2009-28512 A is a two-stage rotational speed increasing handpiece. According to this handpiece, the rotation of drive source is transmitted to the first rotation shaft within the external cylinder. The rotation is further increased by a pair of gears and then transmitted to the second rotation shaft. The increased rotation of the second rotation shaft is transmitted to the treatment tool in the head.

The handpiece disclosed in JP 2005-42883 A is a two-stage speed increasing handpiece in which a rotation of the drive source is firstly transmitted to the rotation shaft within the external housing. The rotation of the first rotation shaft is transmitted and increased through a pair of gears. The increased rotation of the second rotation shaft is further increased and then transmitted to the cutting tool.

Another rotation transmission mechanism with a planetary gear train for transmitting the rotation of the drive source to the head is disclosed in JP 2005-42883 A.

Each of the handpieces disclosed in JP 2005-520580 A and JP 7-51136 B employs an internal gear system in which a distal internal gear of the first rotation shaft is engaged with the associated proximal external gear of the second rotation shaft, which ensures an elevated contact or overlap ratio of the gears and, as a result, a smooth engagement thereof to reduce gear noise. It has been known that the contact ratio indicates the number of simultaneously engaging gear pairs in two engaging gears and the elevated contact ratio ensures that the rotational force being transmitted is divided by more gears and, as a result, the rotation is transmitted from one gear to the other smoothly. This in turn reduces wearing of each gear. Therefore, it is preferably that the contact ratio be equal to or more than 1.0, more preferably, equal to or more than 1.2 from a practical point of view.

According to the handpieces disclosed in JP 2005-520580 A and JP 7-51136 B, the second and third shafts are drivingly connected by the external distal and proximal gears thereof, which makes it difficult to provide an elevated contact ratio for the gear system. This means that each engaging tooth bears a larger load or bending force, which fails to attain a stable engagement of the gears. This also increases the noise, wearing, and damages of the tooth.

Also, increasing the diameters of the external gears to increase the contact ratio of the gears results in an unwanted enlargement of the bending portion of the handpiece, accommodating the external gears, which makes it difficult for operators or users of the handpiece to grip it stably or to operate the handpiece as they like. This in turn may result in that the handpiece touches another tooth or teeth of the patient during cutting treatments.

Further, in the medical or dental handpiece disclosed in JP 2009-28512 A, in order to rotate the cutting tool at an elevated high speed, the teeth number of the small external gear is designed to be considerably smaller to that of the large internal gear. This increases a backlash between the gears, which increases gear noise and stress acting on the teeth and decreases durability of the teeth.

The transmission mechanism disclosed in JP 2005-42883 A employs the planetary gear mechanism, which complicates its mechanical structure.

Therefore, it is an object of the present invention to solve those problems and to provide an easy-to-use medical or dental handpiece having an enlarged contact ratio tooth along with an enlarged tooth thickness, ensuring a stable engagement between the gears, an increased durability of the gears, and an elevated rotation number of the cutting tool.

SUMMARY OF THE INVENTION

In order to achieve the foregoing object, the present invention provides a medical or dental handpiece having a contra-angled grip and a head, the head being mounted at a distal end of the grip, the head being adapted to releasably hold an elongate tool for rotation about a longitudinal axis thereof, comprising:

first, second, and third shafts mounted for rotation about respective longitudinal axes thereof within an internal cavity defined in the grip;

a first gear mechanism for transmitting a rotation from the first shaft to the second shaft; and a second gear mechanism for transmitting the rotation from said second shaft to the third shaft;

each of the first and second gear mechanism having an internal gear and an external gear engaging with the internal gear;

the external gear being substantially enclosed within an assumed cylindrical plane extending along an external peripheral edge of the internal gear.

Preferably, the first gear mechanism has a first axis angle and the second gear mechanism has a second axis angle, at least one of the first and second axis angles being an obtuse angle.

Preferably, the internal gear is defined by a first pitch cone having a first cone angle. Also, the internal gear is defined by a first pitch cone having a first cone angle. Further, the external gear is defined by a second pitch cone having a second cone angle, the second cone angle being smaller than the first cone angle. Then, the internal and external gears are so arranged that apexes of the first and second pitch cones take the same position, and the second pitch cone is inscribed in the first pitch cone.

Preferably, the internal gear of at least one of the first and second gear mechanism has tooth surface portions which appear to be concaved when viewed along general lines of the first pitch cone.

Preferably, in the first gear mechanism the internal gear is mounted on the first shaft and the external gear is mounted on the second shaft and in the second gear mechanism the internal gear is mounted on the second shaft and the external gear is mounted on the third shaft.

Preferably, the head holds a rotor rotatably mounted in the head for releasably holding the tool, the rotor having a rotor gear integrally mounted on the rotor. Also, the third shaft has another gear which engages with the rotor gear. Further, the rotor gear and the another gear constitute the third gear mechanism. Furthermore, the rotor gear has more gears than the another gear. Then, the internal and external gears are so arranged that apexes of the first and second pitch cones take the same position, and the second pitch cone is inscribed in the first pitch cone.

Preferably, at least one of the first to third shafts is made of a hollow tube for transporting fluid.

According to the invention, a thickness of each tooth of the gears in the first and second gear mechanisms is increased. Also, the engagements of the associated tooth surfaces are improved, which ensures that a rotational force is well transmitted from the drive gear to the driven gear. Eventually, the invention reduces gear noise, increases a durability of the gear mechanism, and allows a gear design with an improved strength.

The external diameter of the internal gear can be minimized provided that the external gear engages with the internal gear, which minimizes the external size of the grip and, as a result, ensures the handpiece to be gripped firmly and prevents the grip from being making contacts with the patient, for example, his or her tooth or teeth under treatment.

The rotation of the treatment tool can be increased significantly by the first and second gear mechanisms and then reduced by the third gear mechanism, which reduces a height of the head while keeping the same tooth thickness for the gears.

BRIEF DESCRIPTION OF THE DRAWINGS

The present invention will become more fully understood from the detailed description and the accompanying drawings, wherein:

FIGS. 5A and 5B are diagrams showing axis angles of the drive and driven gears of the first gear mechanism;

FIGS. 6A and 6B are diagrams showing tooth configurations of the drive and driven gears of the first gear mechanism.

DETAILED DESCRIPTION OF THE PREFERRED EMBODIMENTS

Figure 1:
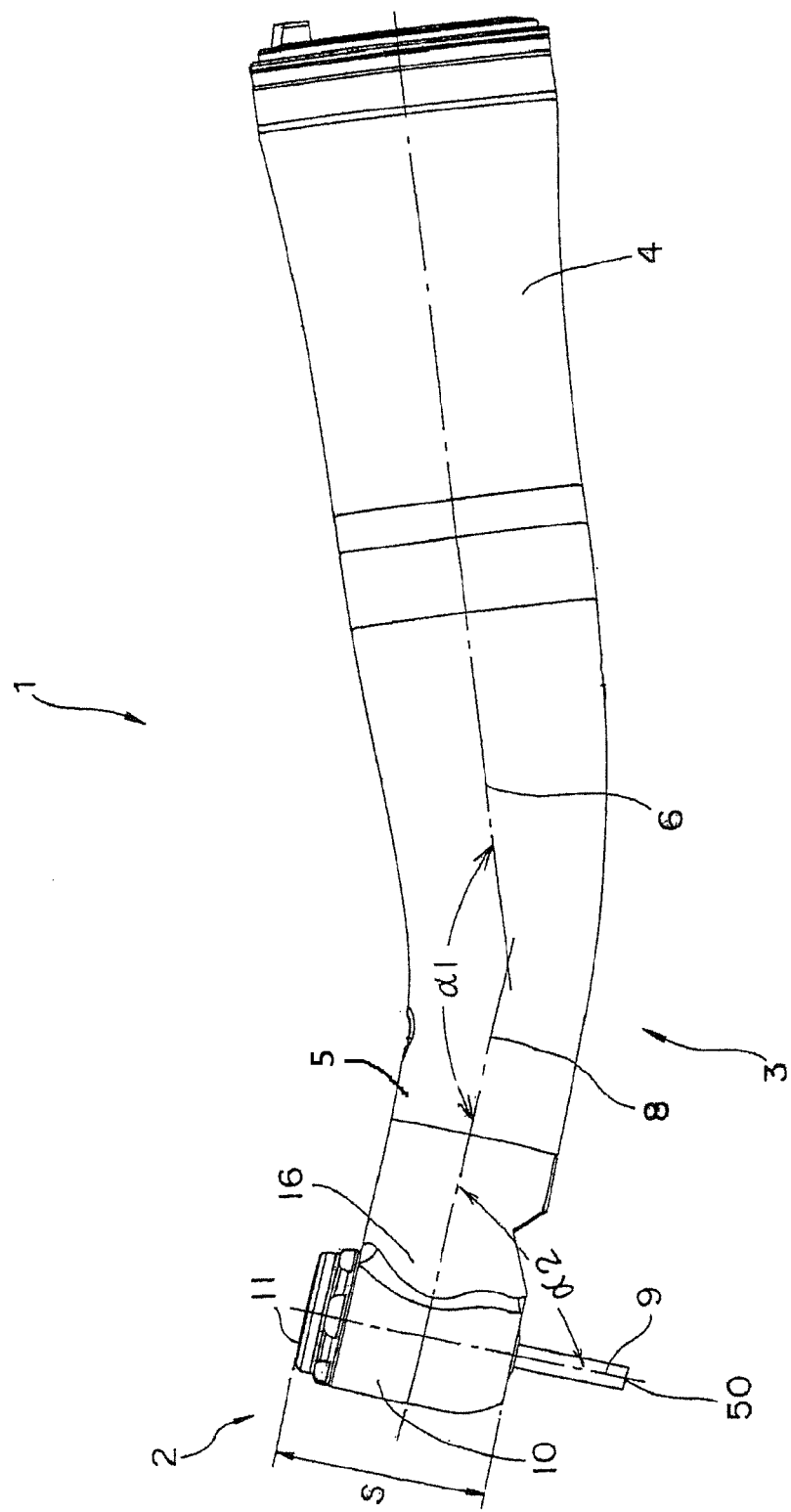
FIG. 1 is a side elevation of a handpiece according to an embodiment of the invention.

The following descriptions of the preferred embodiments are merely exemplary in nature and are in no way intended to limit the invention, its application, or uses.

Hereinafter, preferred embodiments of the present invention will be described with reference to the accompanying drawings.

Referring now to the drawings, a medical or dental handpiece according to an embodiment of the present invention will be described below. Although various languages indicating specific directions such as "distal" and "proximal" will be used in the following descriptions for the better understanding of the invention, the technical scope of the invention should not be construed in a limited way by the use of those languages.

General Construction

Figure 2:
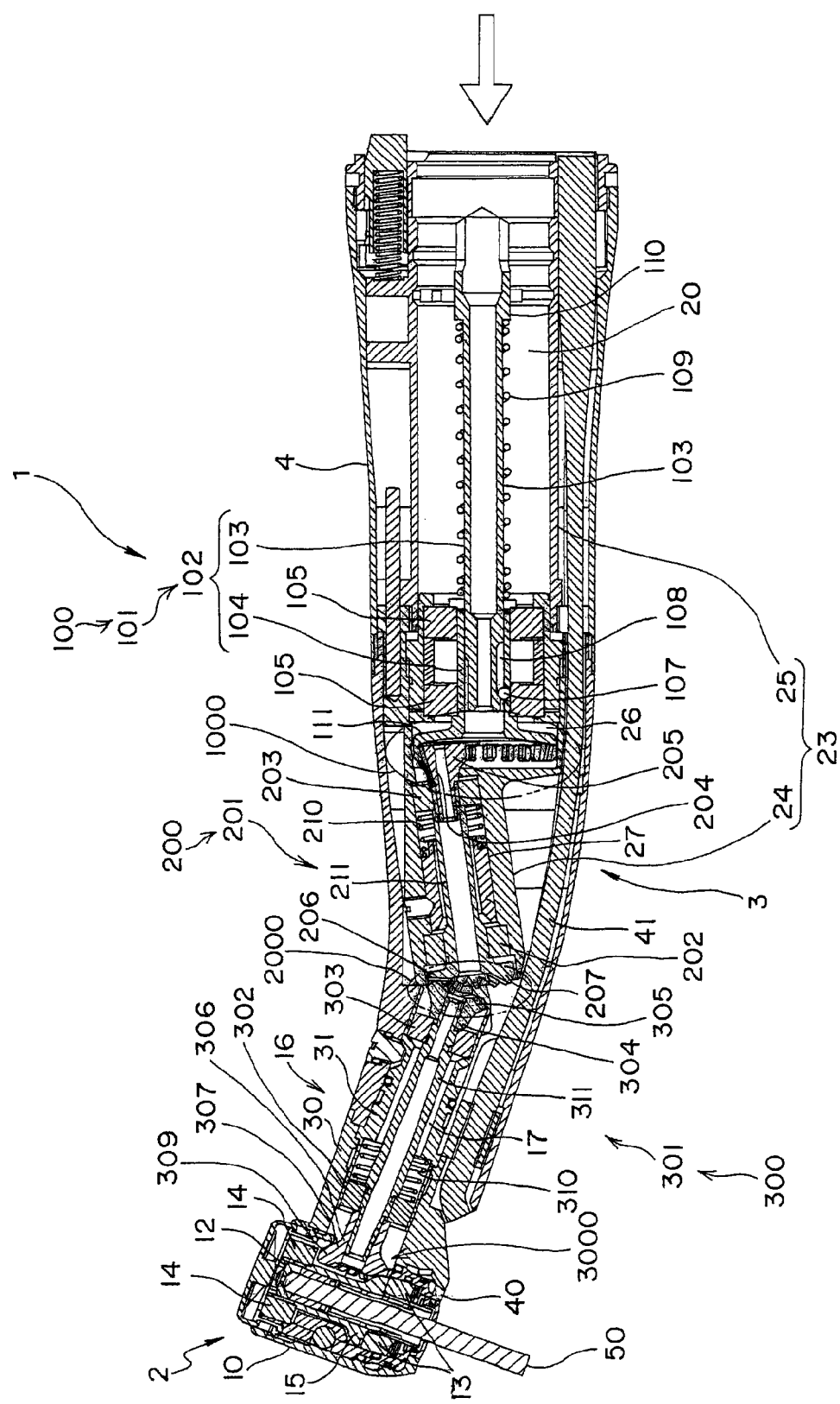
FIG. 2 is a longitudinal cross section of the handpiece shown in FIG. 1.
Figure 3:
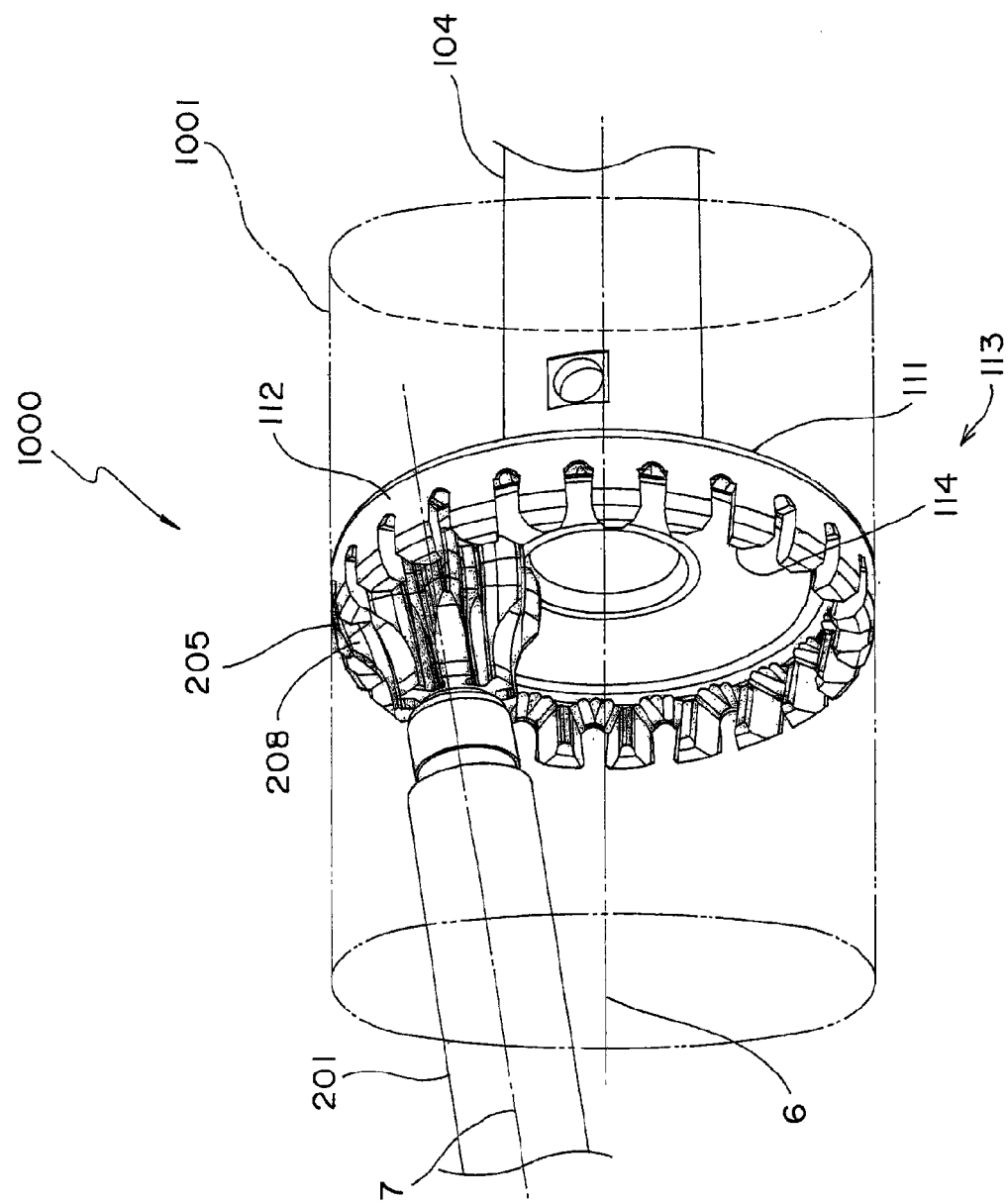
FIG. 3 is a diagram showing an engagement of drive and driven gears of the first gear mechanism.

Referring to FIGS. 1 to 3, the medical or dental handpiece (hereinafter referred to as "handpiece") according to the embodiment of the invention, generally indicated by reference numeral 1, is a contra-angle handpiece. The handpiece 1 has a head 2 and a grip 3 shown on the left and right sides of the drawings, respectively. The head 2 is so configured that various cutting tools 50 can be releasably fitted in the head 2. The grip 3, which is gripped by medical or dental operators or users of the handpiece (e.g., dentists and dental hygienists), is contra-angled and has a proximal external cylinder 4 and a distal external cylinder 5 connected to the distal end of the proximal external cylinder 4. As shown in the drawings, the central axis 6 of the proximal external cylinder 4 intersects at a certain angle with the central axis 8 of the distal external cylinder 5. An angle α1, which is a supplemental angle defined by an extended line of the proximal central axis 6 passing through the intersection and the distal central axis 8 running from the intersection toward the head portion of the handpiece, ranges from 90 to 180 degrees. An angle α2, which is defined by the distal central axis 8 and the central axis of the head 2 (which coincides with the central axis of the cutting tool 50), has about 90 degrees.

The head 2 has a hollow cylindrical housing 10. The housing 10 has a top opening which is closed by a releasable cap 11. The housing 10 accommodates a rotor 12 with a chuck mechanism for chucking or holding the cutting tool 50 along the central axis 9 of the head 2, and bearings 13 and 14 for rotatably supporting the rotor 12. The rotor 12, which is in the form of cylinder, has a rotor gear 15 made of bevel gear integrally formed on its lower external peripheral surface, having a number of teeth arranged on a circle around the central axis 9.

The head 2 has a connecting portion 16 formed integrally with the housing 10 and extending toward the distal end of the handpiece, to which the grip 3 is releasably connected. As shown in the drawing, the connecting portion 16 and the grip 3 are made in the form of hollow cylinders. Then, the connecting portion 16 has a cavity 17 extending along the distal central axis 8. The grip 3 has hollow members, i.e., proximal external hollow portion 4 and distal external hollow portion 5, and the distal end of the distal external hollow portion 5 is releasably connected to proximal end of the connecting portion 16, so that cavities 20 and 26 of the distal and proximal hollow members cooperates with the cavity 17 of the connecting portion 16 to define a space for accommodating a rotation transmission mechanism which will be described below.

Rotation Transmission Mechanism

The rotation transmission mechanism has three, first to third rotation transmission units 100, 200, and 300. According to the embodiment, the first and second rotation transmission units 100 and 200 are positioned by cylindrical positioning means 23 fixedly mounted within respective cavities 20 and 26 defined in the proximal and distal external cylindrical portions 4 and 5. The positioning means 23 is made of distal and proximal cylindrical positioning members 24 and 25. Preferably, the components of the rotation transmission mechanism are made of high intensity and high hardness martensite stainless steel such as SUS 420J2 or SUS440C.

First Rotation Transmission Unit 100

The first rotation transmission unit 100 has a first rotation member 101. The first rotation axis member 101 has a first shaft 102 arranged along the proximal central axis 6 of the grip 3. The first shaft 102 has two hollow shaft members, i.e., proximal shaft member 103 and distal shaft member 104 externally mounted on the distal end of the proximal shaft member 103. The distal shaft member 104 is supported for rotation by a bearing 105 secured within the cavity 26 of the distal positioning member 24. The proximal shaft member 103 is fitted in the distal shaft member 104 so that the proximal shaft member 103 is incapable of rotating about the central axis 6 but capable of moving in the axis direction, relative to the distal shaft member 104. To this end, as shown in FIG. 2, according to the embodiment, the distal shaft member 104 has a though hole 106 for accommodating a ball 107 which is engaged with an associated thrust groove 108 formed on the external periphery of the proximal shaft member 103 and extending in the axial direction. A helical spring 109 is mounted on the periphery of the proximal shaft member 103 so that its distal end abuts the bearing 105 at its distal end and its proximal end abuts the peripheral projections 110 of the proximal shaft member 103, which results in that the proximal shaft member 103 is forced proximally relative to the distal shaft member 104.

The distal end of the distal shaft member 104 has a first flange 111 extending radially outwardly, a second flange 112 extending distally from a peripheral edge of the first flange 111, and an internal gear or drive gear 113 formed on the proximal end of the second flange 112. As shown in detail in FIG. 3, the drive gear 113 has a number of teeth 114 formed at regular intervals in the peripheral direction. Details of the drive gear 113, in particular structure of the teeth 114, will be described below.

Second Rotation Transmission Unit 200

Figure 4:
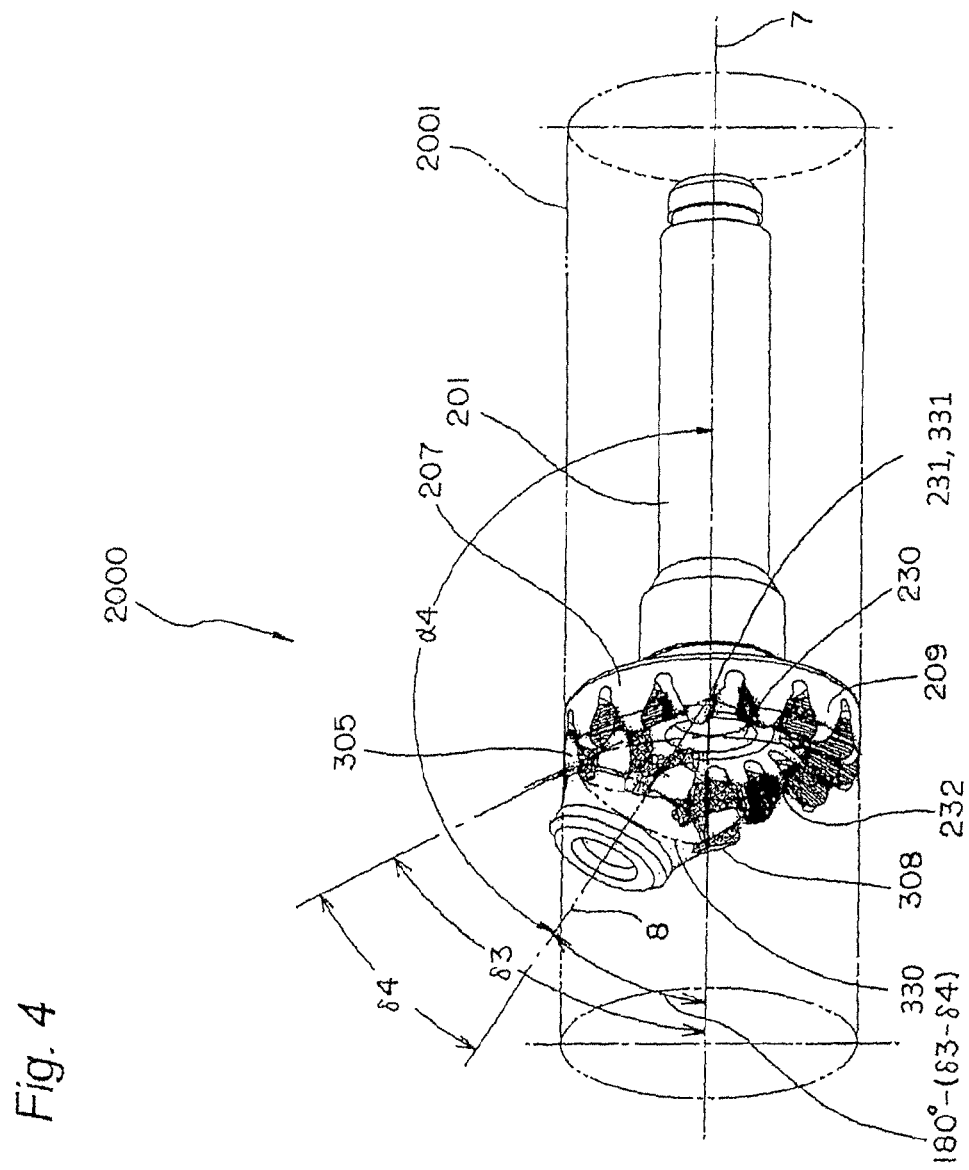
FIG. 4 is a diagram showing an engagement of drive and driven gears of the second gear mechanism and a pitch cone angle of drive gear of the second gear mechanism.

The second rotation transmission unit 200 has a second rotation member 201 made of a hollow tube. The second rotation member 201 is supported for rotation within the distal cavity 27 of the head positioning member 24 through distal and proximal bearings 202 and 203. As shown, the proximal and distal cavities 26 and 27 formed in the head positioning member 24 are formed so that central axes thereof intersect with each other at a certain angle α3 on a plane, i.e., cross section indicated in FIG. 2. The proximal end of the second rotation member 201 is enlarged radially outwardly to form an enlarged diameter portion 204 which carries on its peripheral surface a pinion gear 205 made of a number of external teeth. Also, the distal end is enlarged radially outwardly to form an enlarged diameter portion 206 which carries a bevel gear or intermediate drive gear 207 on its distal end. As shown in FIG. 3, the pinion gear 205 has a number of teeth 208 formed thereon at regular intervals around the distal central axis 7 so that the teeth 208 engage with the associated gears 114 of the drive gear 113. Also, as shown in FIG. 4, the intermediate drive gear 207 has a number of teeth 209 formed thereon at regular intervals around the distal central axis 7. In the embodiment, a helical spring 210 is positioned between the distal and proximal bearings 202 and 203, so that the bearings 202 and 203 are positioned against the distal positioning member 24.

Third Rotation Transmission Unit 300

The third rotation transmission unit 300 has a third rotation member 301 made of a hollow tube. The third rotation member 301 is accommodated in the cavity 17 with its central axis positioned on the distal central axis 8 and supported for rotation about the distal central axis 8 by the distal and proximal bearings 302 and 303. The third rotation member 301 has diametrically enlarged proximal and distal end portions 304 and 306. The enlarged portions 304 and 306 have gears, i.e., an intermediate drive gear 305 and a front gear 307, formed on peripheries thereof, respectively. As shown in FIG. 4, the intermediate drive gear 305 has a number of teeth 308 arranged at regular intervals on a circle extending around the distal central axis 8 so that the teeth 308 engage with teeth 209 of the intermediate drive gear 207. As shown in FIG. 2, the front gear 307 has a number of teeth 309 arranged at regular intervals on a circle extending around the distal central axis 8 so that the teeth 309 engage with the rotor gear 15. In the embodiment, a helical spring 310 is positioned between the distal and proximal bearings 302 and 303 for forcing and thereby positioning the bearings 302 and 303 against the head connecting portion 16.

Assembling

Discussions will be made to the assembling of the handpiece 1 and, in particular, the assembling of the first to third rotation transmission units 100, 200, and 300. In the assembling, before connecting between the head 2 and the grip 3, the third rotation unit 300 is assembled to the head 2 and the first and second rotation transmission units 100 and 200 are assembled to the grip 3.

As shown in FIG. 2, in the embodiment, the connecting portion 16 of the head 2 has a distal connecting portion 30 formed integrally with the housing 10 and a proximal connecting portion 31 connected to the proximal end of the distal connecting portion 30. The third rotation member 301 has a hollow shaft 311 and gear members releasably connected to the proximal and distal ends of the hollow shaft 311. The gear members are formed with the intermediate drive gear 305 and the front gear 307, respectively. Accordingly, in assembling, the hollow shaft 311 is positioned in the cavity 17 of the proximal connecting portion 31, for example. Next, the proximal bearing 303 is externally mounted on the proximal portion of the hollow shaft 311. Then, the intermediate drive gear 305 is secured thereon. Also, the helical spring 310 and the distal bearing 302 are externally mounted on the distal portion of the hollow shaft 311. Then, the front gear 307 is secured thereon. Further, the proximal connecting portion 31 holding the third rotation member 301 is connected to the distal connecting portion 30 and the front gear 307 is engaged with the rotor gear 15 of the head 2.

The first rotation transmission units 100 and 200 are positioned against the positioning portion 23 before their mountings in the grip 3. To this end, the second rotation member 201 of the second rotation transmission unit 200 has a hollow shaft 211. The hollow shaft 211 carries the intermediate drive gear 207 formed integrally therewith at its distal end and a gear member releasably mounted thereon at its proximal end and integrally formed with the pinion gear 205. Therefore, in assembling, the proximal bearing 203, helical spring 210, and distal bearing 211 are inserted in series into the distal cavity 27 of the positioning member 24 from its distal end opening. Then, the hollow shaft 211 without carrying the pinion gear 205 is inserted in the cavity 27. The inserted members are then fixed. Subsequently, the gear member with the integrally formed pinion gear 205 is secured on the proximal end of the hollow shaft 211 extending from the proximal opening of the cavity 27 of the positioning member 24.

For the first rotation transmission unit 100, the distal shaft member 104 is positioned within the proximal cavity 26 of the distal positioning member 24 and the drive gear 113 of the first rotation member 101 is engaged with the pinion gear 205 of the second rotation member 201 held in position by the positioning member 24. Then, the bearing 105 is mounted on the distal shaft member 104 and the first rotation member 101 is rotatably positioned. The positioning of the distal shaft member 104 of the first rotation member 101 to the distal positioning member 24 may be done before the positioning of the second rotation member 201 to the distal positioning member 24.

Subsequently, the distal end of the proximal shaft member 103 bearing the helical spring 109 therearound is inserted in the proximal end of the distal shaft member 104, so that the proximal shaft member 103 can rotate with the distal shaft member 104 and move in the axial direction relative to the distal shaft member 104. Finally, the distal positioning member 25 is connected to the proximal end of the distal positioning member 24.

The positioning member 23 to which the first and second rotation transmission units 100 and 200 have been assembled is inserted within the distal external cylinder 5 from its proximal end opening and positioned therein. Then, the proximal external cylinder 4 is connected to the proximal end of the distal external cylinder 5 to complete the grip 3.

The grip 3 so assembled is connected to the proximal end of the distal connecting portion 16 so that the intermediate drive gear 207 positioned on the distal end of the second rotation member 201 is engaged with the intermediate drive gear 305 positioned on the proximal end of the third rotation member 301.

In operation, a drive unit with a built-in motor (not shown) is connected to the proximal end of the handpiece as shown by the arrow in FIG. 2 and a drive shaft of the motor is drivingly connected to the proximal shaft member 103 of the first rotation member 101. In this condition, the proximal shaft member 103 is forced proximally by the helical spring 109 and thereby securely connected to the drive shaft of the motor. This allows that the rotation of the drive motor is transmitted through the first, second, and third rotation members 101, 201, and 301 to the rotor 12, rotating the cutting tool 50 fitted in the rotor 12.

A ratio of the rotation number of the cutting tool 50 to that of the motor depends upon the teeth numbers of the gears consisting of the gear mechanism. In the embodiment, the gear mechanism is constituted by the dive gear 113 with 23 teeth, pinion gear 205 with 5 teeth, intermediate drive gear 207 with 11 teeth, intermediate drive gear 305 with 8 teeth, front gear 307 with 11 teeth, and rotor gear 15 with 12 teeth. This arrangement results in that the rotation of the motor is increased at the first gear pair 1000 made of the paired drive and pinion gears 113 and 205 for transmitting rotations from the first rotation member 101 to the second rotation member 201, further at the second gear pair 2000 made of the paired intermediate drive gears 207 and 305 for transmitting rotations from the second rotation member 201 to the third rotation member 301, and then decreased at the third gear pair 3000 made of the paired front and rotor gears 307 and for transmitting rotations from the second rotation member 201 to the third rotation member 301, which eventually results in that the rotation of the motor is, as a whole, increased up to 4.15 times. For example, when the rotation of the motor is 40,000 rpm, it is increased up to 132,000 rpm at the first gear pair 1000 and further increased up to 185,000 rpm at the second gear pair 2000, and finally decreased down to 166,000 rpm at the third gear pair 3000. As described above, the rotation number is decreased at the third gear pair 3000, which reduces mechanical stress to be applied to the front and rotor gears 307 and 15 of the third gear pair 3000 and, as a result, increases a durability of the third gear pair 3000. Also, a smaller gear can be used for the front gear 307, which reduces a height S of the head 2 while maintaining a thickness of the gears, which eventually allows the cutting tool 50 of the handpiece to readily access the back teeth in the cutting operations thereof.

In addition, the handpiece 1 according to the embodiment of the invention has an air ejection nozzle 40 on the bottom wall of the housing 10 of the head 2, opposing the distal end of the cutting tool 50, for the ejection of air toward the distal end of the cutting tool. The air may be conveyed to the nozzle by way of an internal cavity defined in the handpiece 1. Alternatively, when the first to third rotation members 101, 201, and 301 are made of hollow tubes, the internal cavities of the hollow tubes may be used at least a part of the air supply passage. The internal cavities of the first to third rotation members 101, 201, and 301 may be used as passages for supplying lubricant agent for cleaning the handpiece 1. Additionally, a light guide 41 may be provided in the handpiece 1 for illuminating the distal end of the cutting tool 50.

First Feature of Gear Mechanism

A feature of first and second gear pairs 1000 and 2000 will be described below. Referring now to FIG. 3, assume a cylindrical plane 1001 extending around the central axis 6 of the first rotation member 101, along an external periphery of the drive gear 113. In this instance, the teeth 208 of the pinion gear 205 are substantially enclosed within the cylindrical plane 1001. The "substantially" means not only that the teeth 208 are completely enclosed within the cylindrical plane 1001, but also that only a part of the teeth 208 can exist outside the circular plane 1001.

Also assume a cylindrical plane 2001 extending around the central axis 7 of the second rotation member 201, along a periphery of the intermediate drive gear 207. In this instance, the teeth 308 of the intermediate drive gear 305 are substantially enclosed within the cylindrical plane 2001. The "substantially" means not only that the teeth 308 are completely enclosed within the cylindrical plane 2001, but also that only a part of the teeth 308 can exist outside the circular plane 2001.

This arrangement of the first and second gear pairs 1000 and 2000 allows each cavity defined in the grip portion enclosing the gear pair 1000 or 2000 to be minimized. This also allows the grip 3 to be minimized to prevent the grip 3 from making contacts with the patient, in particular, teeth thereof under treatment.

Second Feature of Gear Mechanism

A second feature of the first gear pair 1000 will be described below. Referring to FIG. 5, a first pitch cone 120 of the drive gear 113 of the first gear pair 1000 has its apex 121 positioned on the distal side of the drive gear 112 and on the central axis 6 of the first rotation member 101. Also, a second pitch cone 220 of the pinion gear 205 of the first gear pair 1000 has its apex 221 positioned on the same position as the apex 121 of the first pitch cone 120 on the central axis 6. Further, the first and second pitch cones 120 and 220 are so arranged that the second pitch cone 220 is inscribed in the first pitch cone 120 and also the circular bottom edge 222 of the second pitch cone 220 is inscribed in the first circular bottom edge 122 of the first pitch cone 120. The tooth faces or flanks of the drive and pinion gears 113 and 205, in particular, the tooth surface portions engaging with the pinion and drive gears 105 and 113, respectively, are formed on the planes extending from the apexes 121 and 221. Then, the two gears consisting of the first gear pair, i.e., drive gear 113 and the pinion gear 205, are well engaged with each other, which ensures the rotational force to be efficiently transmitted from the drive gear 113 to the pinion gear 205.

The crossing angle, i.e., axis angle $\alpha 3$, between the central axes 6 and 7 of the first and second rotation members 101 and 201 (see FIG. 5B) is set to be an obtuse angle, ranging from 90 to 180 degrees. In the embodiment, the axis angle $\alpha 3$ is set about 170 degrees. As shown, the axis angle $\alpha 3$ is a supplementary angle of a difference between the pitch cone angles $\delta 1$ and $\delta 2$, i.e., $180-(\delta 1-\delta 2)$ degrees.

Third Feature of Gear Mechanism

As shown in FIG. 4, the third pitch cone 230 of one intermediate drive gear 207 of the second gear pair 2000 has its apex 231 positioned on the central axis 7 of the second rotation member 201, on the proximal side of the intermediate drive gear 207. Also, the fourth pitch cone 330 of the other intermediate drive gear 305 of the second gear pair 2000 has its apex 331 which is positioned at the same point as that of the third pitch cone 230 on the same central axis 7. Further, the fourth pitch cone 330 is inscribed in the third pitch cone 230 and the circular bottom edge 332 of the fourth pitch cone 330 is inscribed in the circular bottom edge 232 of the third pitch cone 230. The tooth surfaces of the intermediate drive gears 207 and 305, in particular, tooth surface portions of one gear engaging with those of the other gear, are formed on planes projecting from the apexes 231 and 331, respectively. This allows that the tooth surfaces of the intermediate drive gears 207 and 305 are well engaged with each other, so that the rotational force is well transmitted from one intermediate drive gear 207 to the other intermediate drive gear 305.

The crossing angle, i.e., axis angle $\alpha 4$ between the central axes 7 and 8 of the second and third rotation members 201 and 301 is set to be an obtuse angle, ranging from 90 to 180 degrees. In the embodiment, the axis angle $\alpha 4$ is set about 160 degrees. Similar to the axis angle $\alpha 3$, the axis angle $\alpha 4$ is a supplementary angle of a difference between the pitch cone angles $\delta 3$ and $\delta 4$, i.e., $180-(\delta 3-\delta 4)$ degrees. Although in the previous embodiment each of the crossing or axis angle $\alpha 3$ between the central axes 6 and 7 of the first and second rotation members 101 and 201 of the first gear pair 1000 and the crossing or axis angle $\alpha 4$ between the central axes 7 and 8 of the second and third rotation members 201 and 301 of the second gear pair 2000 is set to be an obtuse angle ranging from 90 to 180 degrees, it is sufficient that only one of two axis angles of the first and second gear pairs 1000 and 2000 is set to be an obtuse angle ranging from 90 to 180 degrees.

Fourth Feature of Gear Mechanism

FIGS. 6A and 6B show the drive gear 113 of the first gear pair 1000. In particular, FIG. 6B shows teeth 114 of the drive gear when viewed from the distal side and along the cone generating lines 124 of the pitch cone 120. As shown in the drawing, the tooth surfaces 125 of the drive gear 113 engaging with the pinion gear 205, in particular, tooth surface portions extending from roots 126 to apexes 127 shown in the cross section taken along line VI-VI in FIG. 6A and perpendicular to the cone general lines 124 of the pitch cone 120, are concaved inwardly. Contrary to this, similar to the conventional gears, the tooth surfaces of the pinion gear 205 engaging with the drive gear 113 are convexed outwardly. Alternatively, the convexed tooth surfaces may have an involute profile.

Although not shown, in the second and/or third gear pair 2000 and/or 3000, the driven gear thereof employs the outwardly convexed profile for its tooth surfaces and the drive gear thereof employs complementary inwardly concaved profile for its tooth surfaces. Further, the convexed tooth surfaces of the driven gear may be invluted.

For gears with concaved tooth surfaces and with planar tooth surfaces (i.e., not-convexed and not-concaved tooth surfaces), a maximum shear stress (Von Mises maximum shear stress) applied to each tooth engaging with the gear with convexed tooth surfaces was calculated using the finite element method. The result showed that the maximum shear stress applied on the planar tooth surface was about 1.2 times as much as that applied on the concaved tooth surface, which means that the concaved tooth surface of the drive gear extend the service life of the gears.

Figure 7:
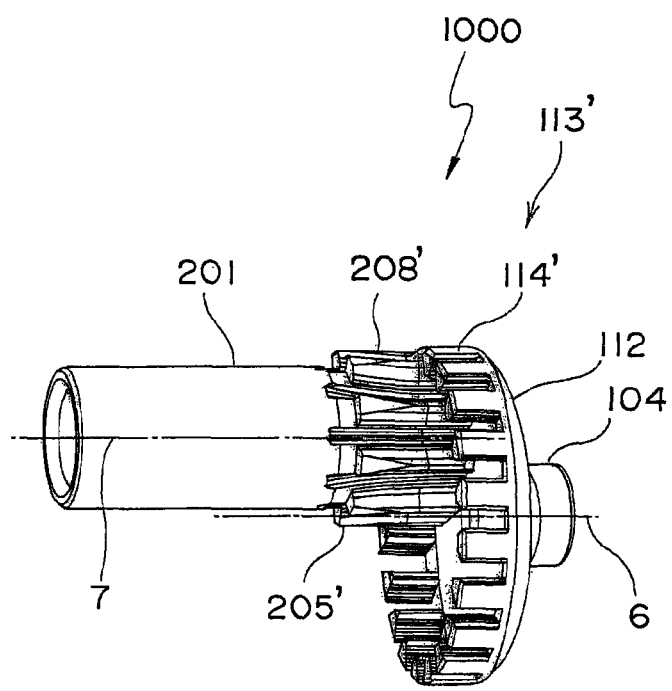
FIG. 7 is a perspective view showing a first gear mechanism of a handpiece according to another embodiment in which a central axis of the drive gear is parallel to that of the driven gear.

Although in the previous embodiment the central axes of respective gears of the first and second gear pairs are intersected, a pair of internal and external spur gears are used to engage with each other with their central axes positioned in parallel with each other. For example, FIG. 7 shows a modification in which the gear pair is constructed by an internal drive gear 113 having internal teeth 114' of which tooth surfaces extend in parallel to its central axis and an external pinion gear 205' having external teeth 208' engageable with the teeth 114, the internal drive gear 113' and the external pinion gear 205' being engaged with each other with their central axes directed in parallel to each other.

Although not shown, the second gear pair 2000 may also be constituted in the same manner as the first gear pair 1000. In this instance, it is preferable that the portion of each tooth extending from the root 126 to the apex 127 is configured as a concaved curve surface. Each tooth surface of the pinion gear 205' engaging with the drive gear 113' (not shown) may be a convexed or an involuted curve surface.

The description of the invention is merely exemplary in nature and, thus, variations that do not depart from the gist of the invention are intended to be within the scope of the invention. Such variations are not to be regarded as a departure from the spirit and scope of the invention. For example, although there have been described respective embodiments independently, a combination of two or more thereof should be within the scope of the present invention.

What is claimed is:

1. A handpiece having a contra-angled grip and a head, the handpiece comprising:
   first, second, and third shafts mounted for rotation about respective longitudinal axes thereof within an internal cavity defined in the grip;
   a first gear pair for transmitting a rotation from the first shaft to the second shaft; and
   a second gear pair for transmitting the rotation from the second shaft to the third shaft;

the first gear pair having a first internal gear mounted on the first shaft and a first external gear mounted on the second shaft and engaged with the first internal gear; and the second gear pair having a second internal gear mounted on the second shaft and a second external gear mounted on the third shaft and engaged with the second internal gear;

wherein the first internal gear is defined by a first pitch cone having a first cone angle and a first apex;

wherein the first external gear is defined by a second pitch cone having a second cone angle and a second apex;

wherein the first cone angle is greater than the second cone angle; and wherein the first apex and the second apex take the same position.

2. The handpiece of claim 1, wherein the first external gear is substantially enclosed within an assumed first cylindrical plane extending along a first external peripheral edge of the first internal gear; and wherein the second external gear is substantially enclosed within an assumed second cylindrical plane extending along a second external peripheral edge of the second internal gear.

3. The handpiece of claim 1, wherein the second internal gear is defined by a third pitch cone having a third cone angle and a third apex;

wherein the second external gear is defined by a fourth pitch cone having a fourth cone angle and a fourth apex;

wherein the third cone angle is greater than the fourth cone angle; and wherein the third apex and the fourth apex take the same position.

4. The handpiece of claim 3, wherein the fourth pitch cone is inscribed in the third pitch cone.

5. The handpiece of claim 1, wherein the first gear pair has a first axis angle between the longitudinal axis of the first shaft and the longitudinal axis of the second shaft;

wherein the second gear pair has a second axis angle between the longitudinal axis of the second shaft and the longitudinal axis of the third shaft; and wherein at least one of the first and the second axis angles is an obtuse angle.

6. The handpiece of claim 1, wherein the second pitch cone is inscribed in the first pitch cone.

7. The handpiece of claim 1, wherein at least one of the first and the second internal gears has tooth surface portions that are concaved when viewed along cone generating lines of the first pitch cone.

8. The handpiece of claim 1, wherein a head is mounted at a distal end of the grip;

wherein a rotor is rotatably mounted in the head for releasably holding a tool;

wherein a rotor gear is mounted on the rotor;

wherein the third shaft has a third shaft gear engaged with the rotor gear;

wherein the rotor gear and the third shaft gear constitute a third gear pair; and wherein the rotor gear has more teeth than the third shaft gear.

9. The handpiece of claim 1, wherein at least one of the first to third shafts is a hollow tube for transporting fluid.

10. The handpiece of claim 1, wherein the first shaft and the second shaft cross each other at a first predetermined angle, and the second shaft and the third shaft cross each other at a second predetermined angle.

11. The handpiece of claim 1, wherein each of the first and the second internal gears of the first and the second gear pairs is a bevel gear.

* * * * *